United States Patent
Bhagchandani et al.

(10) Patent No.: US 10,159,489 B2
(45) Date of Patent: Dec. 25, 2018

(54) SYSTEMS AND METHODS FOR DELIVERING MULTIPLE EMBOLIZATION COILS

(71) Applicant: Cook Medical Technologies LLC, Bloomington, IN (US)

(72) Inventors: Neha S. Bhagchandani, Bloomington, IN (US); Vanessa Weisman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/952,695

(22) Filed: Jul. 29, 2013

(65) Prior Publication Data

US 2014/0031858 A1     Jan. 30, 2014

Related U.S. Application Data

(60) Provisional application No. 61/677,165, filed on Jul. 30, 2012.

(51) Int. Cl.
*A61B 17/12*     (2006.01)

(52) U.S. Cl.
CPC .... *A61B 17/1214* (2013.01); *A61B 17/12109* (2013.01); *A61B 17/12113* (2013.01); *A61B 17/1215* (2013.01); *A61B 2017/12054* (2013.01)

(58) Field of Classification Search
CPC ........ A61B 17/12109; A61B 17/12113; A61B 17/1214; A61B 17/1215; A61B 17/12145; A61B 17/12022; A61B 17/12163; A61B 17/12027; A61B 17/12036; A61B 2017/12054; A61B 2017/1205; A61B 12/12154; A61B 17/12099; A61B 17/12104; A61B 17/12118; A61B 17/12122; A61B 17/12031; A61B 17/1204; A61B 17/13131; A61B 2017/12059; A61B 2017/12063; A61B 2017/12068; A61B 2017/12077; A61B 2017/12081; A61B 2017/12086; A61B 2017/1209; A61B 2017/12095; A61B 2017/12072; A61F 2002/826; A61F 2002/9505; A61F 2002/9511; A61F 2002/9665; A61F 2/954; A61F 2/962; A61F 2/966; A61F 2/88; A61F 2/885; A61F 2230/0091

(Continued)

(56) References Cited

U.S. PATENT DOCUMENTS 5,830,230 A      11/1998  Berryman et al.
6,193,708 B1 *   2/2001   Ken ................. A61B 17/12022
                                                      606/1

(Continued)

*Primary Examiner* — Darwin Erezo
*Assistant Examiner* — Katherine Schwiker
(74) *Attorney, Agent, or Firm* — Woodard Emhardt Moriarty McNett & Henry LLP (57) ABSTRACT

Systems and methods for delivering multiple embolization coils to a location within the body of a patient are disclosed. In one embodiment, a coil delivery system has coil deployment members coupled to embolization coils and is arranged for independent movement of the embolization coils. In some exemplary embodiments, the disclosure provides coil delivery systems in which the embolization coils are positioned within different lumens and/or on different straightening members. Methods and other embodiments are disclosed.

22 Claims, 8 Drawing Sheets

(58) Field of Classification Search
USPC .......................................................... 606/191
See application file for complete search history.

(56) References Cited

U.S. PATENT DOCUMENTS

| | | | | |
|---|---|---|---|---|
| 6,428,557 | B1 * | 8/2002 | Hilaire | A61B 17/12022 |
| | | | | 606/200 |
| 6,802,851 | B2 * | 10/2004 | Jones | A61B 17/12022 |
| | | | | 606/200 |
| 7,128,736 | B1 * | 10/2006 | Abrams | A61B 17/12022 |
| | | | | 606/1 |
| 7,377,932 | B2 | 5/2008 | Mitelberg et al. | |
| 7,901,444 | B2 | 3/2011 | Slazas | |
| 2003/0171739 | A1 * | 9/2003 | Murphy | A61B 17/12022 |
| | | | | 606/1 |
| 2004/0098023 | A1 * | 5/2004 | Lee et al. | 606/200 |
| 2007/0083226 | A1 | 4/2007 | Buiser et al. | |
| 2007/0270903 | A1 * | 11/2007 | Davis, III | A61B 17/12022 |
| | | | | 606/200 |
| 2008/0091223 | A1 * | 4/2008 | Pokorney et al. | 606/159 |
| 2008/0281350 | A1 * | 11/2008 | Sepetka | A61B 17/0057 |
| | | | | 606/200 |
| 2009/0054905 | A1 | 2/2009 | Levy | |
| 2010/0004671 | A1 * | 1/2010 | Gerberding | A61B 17/12022 |
| | | | | 606/198 |
| 2010/0010533 | A1 | 1/2010 | Burke et al. | |
| 2010/0185228 | A1 | 7/2010 | Tekulve et al. | |

* cited by examiner

SYSTEMS AND METHODS FOR DELIVERING MULTIPLE EMBOLIZATION COILS

CROSS-REFERENCE TO RELATED APPLICATIONS

This application claims the benefit of U.S. Provisional Application No. 61/677,165, filed Jul. 30, 2012, which is hereby incorporated by reference in its entirety.

FIELD OF THE INVENTION

The present invention relates generally to systems and methods for delivering multiple embolization coils within the body of a patient.

BACKGROUND

Intravascular interventional procedures for providing an artificial embolism are desirable in some patients for controlling internal bleeding, preventing blood supply to tumors, or relieving pressure in the vessel wall near an aneurysm. Several approaches are known for providing an artificial embolism, including the use of an inflatable, detachable balloon or the injection of a coagulative substance. Another approach utilizes an occlusive wire coil, referred to as an embolization coil, and delivery system for positioning the coil at a desirable site in a blood vessel.

In some procedures, multiple embolization coils are used to occlude blood flow. For example, in particularly large aneurysms, multiple embolization coils may be needed to sufficiently fill the aneurysm to relieve pressure in the vessel wall. Similarly, multiple coils may be used to facilitate a certain artificial embolism technique. For example, those using the scaffold technique may place a first coil followed by a second coil, the first coil providing a support ("scaffold") for the second coil.

With some existing embolization coil delivery systems, an operator must load an embolization coil from a coil-loading cartridge into an indwelling catheter. The coil is then pushed through the catheter by a delivery wire until the coil emerges from the distal tip of the catheter and, in some instances, assumes a folded, convoluted configuration. If the operator wishes to deploy a second embolization coil, the operator must load another embolization coil from a coil-loading cartridge into the catheter for delivery and push the second embolization coil out of the distal tip of the catheter.

There exists a need for new systems and methods for delivering multiple embolization coils.

SUMMARY

In certain aspects, the present disclosure provides systems and methods capable of delivering multiple embolization coils to a location within the body of a patient. In accordance with some forms of the invention, such systems and methods are preloaded with embolization coils and are configured to deploy multiple embolization coils without having to reload the system.

In some embodiments, the present disclosure teaches a multi-embolization coil delivery system comprising: an elongated body retaining a first embolization coil, a second embolization coil, a first coil deployment member, and a second coil deployment member; the first embolization coil coupled to the first coil deployment member; and the second embolization coil coupled to the second coil deployment member; wherein the first coil deployment member is independently manipulable of the second coil deployment member. In some instances, the delivery system further comprises a first lumen defined by the elongated body; a second lumen defined by the elongated body; the first embolization coil positioned in the first lumen; and the second embolization coil positioned in the second lumen. Additionally, or alternatively, some embodiments include a system wherein the first and second embolization coils are capable of movement independent of one another.

In some instances, the present disclosure teaches a multi-embolization coil delivery system, comprising: an elongated body arranged to retain a first embolization coil and a second embolization coil; and the first embolization coil longitudinally spaced from the second embolization coil; wherein the delivery system is operable to move the first embolization coil independently of the second embolization coil. In some instances, the delivery system further comprises a first lumen defined by the elongated body; a second lumen defined by the elongated body; the first embolization coil positioned in the first lumen; and the second embolization coil positioned in the second lumen. Additionally, or alternatively, some embodiments include a system wherein the first embolization coil is a scaffold embolization coil and is positioned distally of the second embolization coil.

Additionally, the present disclosure teaches a multi-embolization coil delivery system, comprising: an elongated body defining a first lumen and a second lumen; a first embolization coil positioned in the first lumen; and a second embolization coil positioned in the second lumen. In some embodiments, the first embolization coil and the second embolization coil have a different frequency of turns in the coils in their insertable and/or deployed configurations, and/or have different properties. For example, the coils may be constructed of different materials. Additionally, or alternatively, in some instances the first embolization coil is a scaffold embolization coil and is positioned distally of the second embolization coil.

Further forms, objects, features, aspects, benefits, advantages, and embodiments of the present invention will become apparent from a detailed description and drawings provided herewith.

DESCRIPTION OF THE ILLUSTRATED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will likely first appear in FIG. 1, an element identified by a "200" series reference numeral will likely first appear in FIG. 2, and so on.

The disclosed embodiments and variations thereof may be used to deliver implantable devices, such as embolization coils, to locations within the body of a human and/or veterinary patient. For instance, the disclosed embodiments may be used to delivery embolization coils to a location within a vessel of a patient's limb, abdomen, chest, and/or brain. For simplicity, the following embodiments will be illustrated with reference to the deployment of an embolization coil into a blood vessel and/or aneurysm sac of a patient; however, it is not intended that the present disclosure be limited to such. Other implantable devices may be deployed using some of concepts and embodiments disclosed herein, and the deployment of implantable devices at other target locations within the body of a patient is also contemplated.

The present disclosure provides systems and methods for delivering coils to one or more target locations in the body of a patient. As illustrated in the figures accompanying this description, some embodiments of the present disclosure provide a coil delivery system that is arranged to deliver one or more embolization coils. Specifically, some embodiments comprise an embolization coil having a wire portion, a fiber portion, and/or configurable from an insertable configuration into a deployed configuration. For example, a first embolization coil 50 can have a wire portion 52 and a fiber portion 54. In an insertable configuration, the first embolization coil may also define a coil lumen 56. The first embolization coil 50 may be of the type referred to as a "scaffold" type coil that is arranged to provide support for subsequent embolization coils.

In some instances, the coil delivery system comprises a second embolization coil 60 that is configurable between an insertable configuration and a deployed configuration and defines a coil lumen 66 in an insertable configuration. The second embolization coil 60 may be of the type referred to as a "packing" type coil that is arranged to deploy in combination with a scaffold type coil to provide support thereof. For example, a scaffolding coil can be deployed to a target location and then a packing coil can be deployed in the same area as the scaffolding coil such that the scaffolding coil provides support for the packing coil and the packing coil provides a greater degree of cross-sectional occlusion to improve thrombogenicity of the implanted system. In various embodiments disclosed hereafter, reference will be made to embolization coils 50 and 60 and parts thereof.

Figure 1:
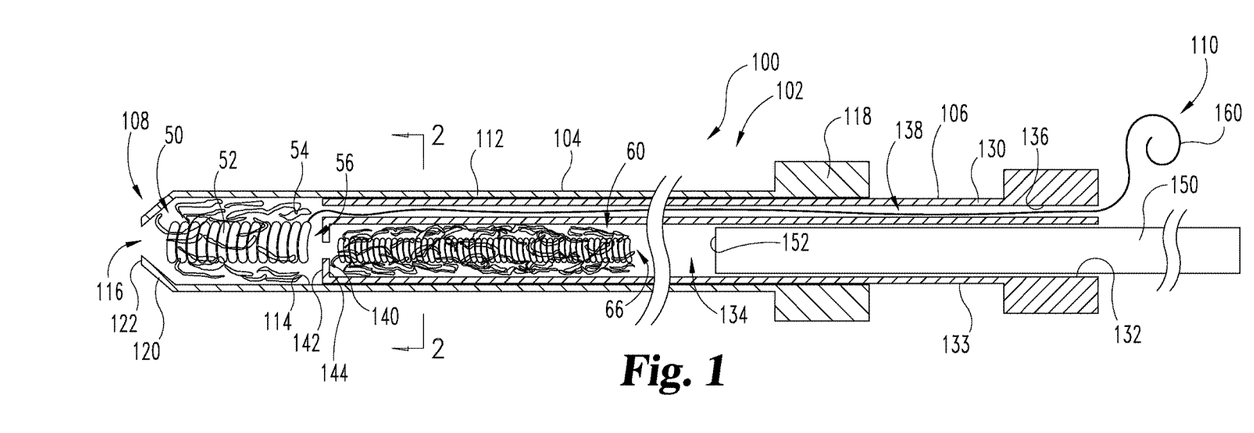
FIG. 1 illustrates an embodiment of an embolization coil delivery system.
Figure 2:
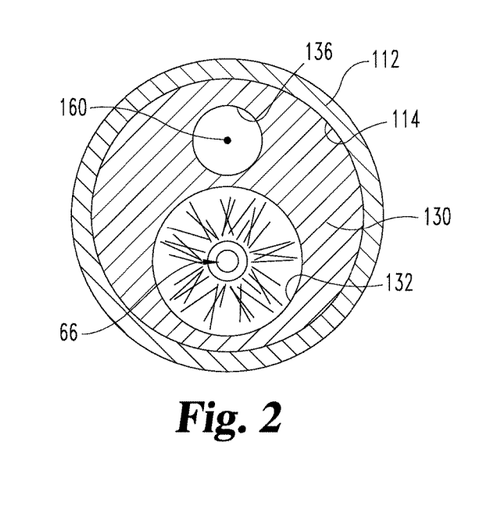
FIG. 2 is a cross-sectional view of the embolization coil delivery system illustrated in FIG. 1.

FIGS. 1 and 2 illustrate one embodiment of a coil delivery system 100. The coil delivery system 100 comprises an elongated body 102 having an outer cannula 104, an inner cannula 106, a distal end region 108 and a proximal end region 110. The outer cannula 104 has a wall 112 that has an inside surface 114 defining an outer cannula lumen 116. As illustrated in FIGS. 1 and 2, a first embolization coil 50 may be positioned within the outer cannula lumen 116 near the distal end region 108 of the elongated body 102. The outer cannula 104 may also have a handle portion 118 arranged to be grasped by the hand of an operator.

In some embodiments, the wall 112 of the outer cannula 104 has a tapered portion 120 at its distal end region so as to aid in the insertion of the outer cannula 104 into the body of a patient without causing trauma to the inside of a vessel. Additionally, in some instances, the tapered portion 120 may aid in preventing a premature release of the first embolization coil 50 from within the coil delivery system 100.

The inner cannula 106 is slidably positioned within the outer cannula lumen 116. The inner cannula 106 has a wall 130 with an inner surface 132 that defines a coil lumen 134 and an outer surface 133 that is slidably coupled to the inside surface 114 of the wall 112 of the outer cannula 104. Additionally, the inner cannula 106 has a surface 136 that defines a coupling member lumen 138.

In some embodiments, the wall 130 of the inner cannula 106 has portions arranged to push the first embolization coil 50 through and/or out of the outer cannula lumen 116. For example, the inner cannula 106 can have a flange portion 140 with a distal surface 142 and a proximal surface 144. The distal surface 142 is arranged to pushably couple to a proximal portion of the first embolization coil 50 such that the inner cannula 106 can push the first embolization coil 50 through and/or out of the outer cannula lumen 116. In some instances, the proximal surface 144 of the flange portion 140 of the inner cannula 106 is arranged to prevent the premature release of the second embolization coil 60 from within the coil lumen 134 of the inner cannula 106. For example, the proximal surface 144 of the flange portion 140 may extend inwards from the inner surface 132, e.g., towards the middle of the coil lumen 134, and face the second embolization coil 60, and if the second embolization coil 60 slides distally in the coil lumen 134, a portion of the second embolization coil 60, such as the fibers, can contact the proximal surface 144 of the flange portion 140 and prevent the second embolization coil 60 from exiting the coil lumen 134.

A coil deployment member, such as a pushing member 150 is slidably positioned within the coil lumen 134 proximal of the second embolization coil 60. The pushing member 150 has a pushing surface 152 on a distal end of the pushing member 150. The pushing surface 152 is arranged to pushably couple to a proximal portion of the second embolization coil 60 such that the pushing member 150 can push the second embolization coil 60 out of the coil lumen 134 of the inner cannula 106.

In some embodiments, a proximal portion of the pushing member 150 extends past a proximal end of the outer cannula 104 and/or the inner cannula 106. Additionally, in some instances the pushing member 150 has a portion arranged to be manipulated by the hand of an operator so as to slide the pushing member 150 through the coil lumen 134 of the inner cannula 106.

Another coil-deployment member, such as a coupling member 160, is coupled to a portion of the first embolization coil 50 and extends from the first embolization coil 50 through the coupling member lumen 138 of the inner cannula 106 towards the proximal end region 110 of the elongated body 102. The coupling member 160 has a proximal portion arranged to be manipulable by an operator of the coil delivery system 100 such that the operator can manipulate the coupling member 160 to detach a portion of the coupling member 160 from the first embolization coil 50. In some instances, the coupling member 160 extends a distance away from the proximal end region 110 of the elongated body 102.

The coupling member 160 can be arranged so as to retain the first embolization coil 50 prior to the desired deployment. For example, the coupling member 160 may retain a portion of the first embolization coil 50 within the outer cannula lumen 116. In some instances, the coupling member 160 couples the first embolization coil 50 to a distal portion of the inner cannula 106 so that the inner cannula 106 is capable of moving the first embolization coil 50 in a distal or proximal direction through and/or out of the outer cannula lumen 116, such as by pushing and pulling. Similarly, in some embodiments, the coupling member 160 is coupled to and arranged to move the first embolization coil 50 through and/or into the outer cannula lumen 116. In some instances, the coupling member 160 may be used to withdraw a deployed portion of the first embolization coil 50 back into the outer cannula lumen 116.

In some embodiments, the coupling member 160 is arranged to allow an operator to reposition a portion of a deployed embolization coil. For example, after the first embolization coil 50 is deployed and prior to detachment of the coupling member 160 from the first embolization coil 50, an operator can manipulate a portion of the coupling member 160 to move a portion of the first embolization coil 50 that is positioned outside of the outer cannula lumen 116 and coupled to the coupling member 160. The coupling member 160 can be arranged to allow an operator to pull a portion of the first embolization coil 50 through the vessel in a proximal direction. Additionally, the coupling member 160 can be arranged to couple a portion of the first embolization coil 50 to the distal surface 122 of the wall 112 of the outer cannula 104, allowing an operator to push a portion of the first embolization coil 50 through the vessel in a distal direction.

As will be appreciated by one of ordinary skill in the art, the coupling member 160 may be coupled to a portion of the first embolization coil 50 in any number of ways. For example, the coupling member 160 may be attached to the wire portion 52 of the first embolization coil 50 by an adhesive and/or by compressing the coupling member 160 between coil portions of the wire portion 52, similar to the manner in which the fiber portion 54 may be attached to the wire portion 52. Similarly, for coupling members 160 that are elongate flexible members such as sutures, the coupling member 160 may be tied around a portion of the first embolization coil 50. In several instances, the coupling member 160 is detachably coupled to the first embolization coil 50.

Similarly, the coupling member 160 may be arranged so that a portion of the coupling member 160 may be detached and/or released from the first embolization coil 50 in any number of ways. In some instances, the coupling member 160 is arranged to release from the first embolization coil 50 when a force above an upper threshold is applied to the coupling member 160. For example, the coupling member 160 may be tied into a knot that will release, e.g., untie, upon a certain force, or the coupling member 160 may be removed from a compressed position between the coils of the wire portion 52, to name a few non-limiting examples. In other instances, the coupling member 160 may have a portion arranged to break and/or sever so as to decouple a proximal portion of the coupling member 160 from a distal portion of the coupling member 160 and/or the first embolization coil 50. In some instances, the distal surface 122 of the tapered portion 120 of the outer cannula 104 and/or a portion of the inner cannula 106 may be used to restrict a portion of the first embolization coil 50 from entering the outer cannula lumen 116 so that sufficient tensile force may be applied to the coupling member 160 so as to decouple the coupling member 160 from the first embolization coil 50.

Figure 3:
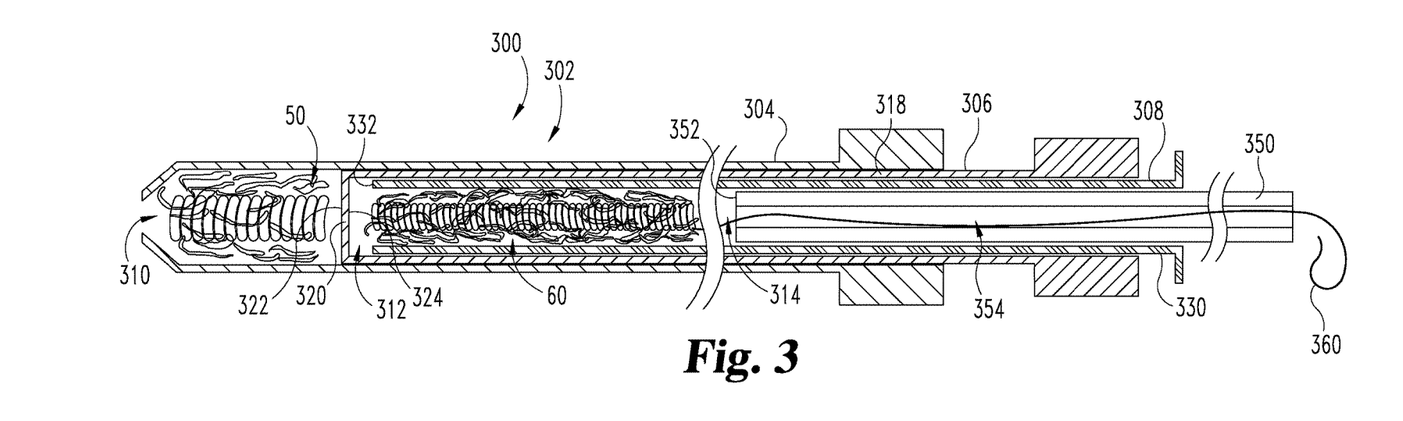
FIG. 3 illustrates an embodiment of an embolization coil delivery system.

FIG. 3 illustrates another embodiment of a coil delivery system 300 having an elongated body 302 with an outer cannula 304, an intermediate cannula 306, and an inner cannula 308. The outer cannula 304 defines an outer lumen 310 with the intermediate cannula 306 and a first embolization coil 50 being slidably positioned within the outer lumen 310, the first embolization coil 50 positioned distal of the intermediate cannula 306.

The intermediate cannula 306 has a wall portion 318 with a surface that defines the intermediate lumen 312. The intermediate cannula 306 also has a door portion 320 near the distal end of the intermediate cannula 306. The door portion 320 has a distal surface 322 and a proximal surface 324. The distal surface 322 of the door portion 320 faces in a distal direction and is arranged to contact a proximal portion of the embolization coil 50 positioned within the outer lumen 310. The distal surface 322 can be arranged to pushably couple to a proximal portion of the first embolization coil 50 such that the door portion 320 of the intermediate cannula 306 may push the embolization coil 50 through and/or out of the outer lumen 310 of the coil delivery system 300.

The door portion 320 of the intermediate cannula 306 can be pivotably coupled to the wall portion 318. In some embodiments, the door portion 320 is arranged such that upon a force on the proximal surface 324, the door portion 320 rotates away from the intermediate lumen 312 into a position adjacent to the inner surface of the outer cannula 304.

An inner cannula 308 is positioned within the intermediate lumen 312 of the intermediate cannula 306. The inner cannula 308 defines an inner lumen 314 having a second embolization coil 60 and a pushing member 350 positioned therein.

The inner cannula 308 has a wall 330 with a pushing surface 332 on a distal end of the inner cannula 308. The pushing surface 332 is arranged to contact the proximal surface 324 of the door portion 320 of the intermediate cannula 306 so as to push the door portion 320 into an open position, e.g., against the surface of the outer cannula 304 that defines the outer lumen 310. Positioning the door portion 320 into an open position allows for communication between the intermediate lumen 312, the inner lumen 314, and the outer lumen 310 and also allows the inner cannula 308 to be slidably positioned within the outer lumen 310.

A pushing member 350 is positioned within the inner lumen 314 of the inner cannula 308. The pushing member 350 has a pushing surface 352 on a distal end. The pushing surface 352 is arranged to contact a proximal portion of the second embolization coil 60 such that the pushing surface 352 can push the second embolization coil 60 out of the inner lumen 314, the intermediate lumen 312, and/or the outer lumen 310 of the coil delivery system 300.

Additionally, in some embodiments, the pushing member 350 may define a coupling member lumen 354 arranged to receive a coupling member 360. The coupling member lumen 354 may extend from a distal end to a proximal end of the pushing member 350, and the coupling member 360 may couple to a proximal end of the second embolization coil 60 and extend proximally through the coupling member lumen 354 and out of the proximal end of the pushing member 350 so as to have a portion that is accessible and manipulable by an operator of the coil delivery system 300.

Figure 4:
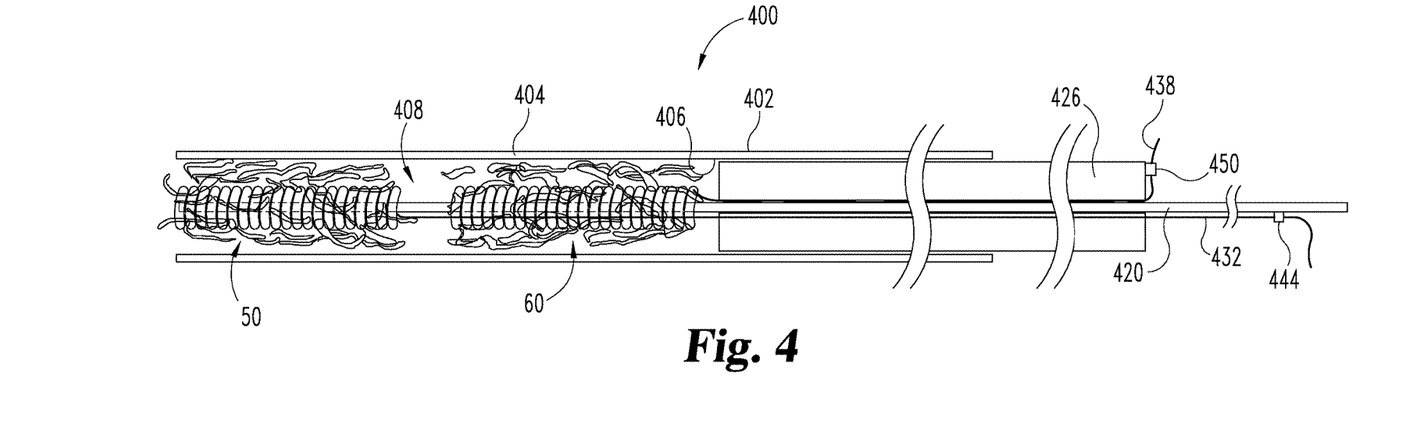
FIG. 4 illustrates an embodiment of an embolization coil delivery system.

FIG. 4 illustrates a cross-sectional view of another embodiment of a coil delivery system 400. A coil delivery system 400 may comprise a catheter 402 having a wall portion 404 with an inner surface 406 that defines a lumen 408. Positioned within the lumen 408 is a first pushing member 420 extending from a proximal end region of the coil delivery system 400 through a lumen defined by a second pushing member 426 and through the coil lumen 66 of the second embolization coil 60 to the first embolization coil 50 positioned at a distal end region of the coil delivery system 400.

In some instances, the first pushing member 420 is slidably coupled to the second pushing member 426 and/or the second embolization coil 60 such that the first pushing member 420 can slide through the lumen defined by the second pushing member 426 and the coil lumen 66 independently of the movement of the second pushing member 426 and the second embolization coil 60.

In some instances, the first pushing member 420 is pushably coupled to a proximal end of the first embolization coil 50 such that the first pushing member 420 can push the first embolization coil 50 out of the lumen 408 of the catheter 402. In other embodiments, the first pushing member 420 extends through a portion of the coil lumen 56 of the first embolization coil 50 towards a distal end of the first embolization coil 50 and is pushably coupled to a portion of the first embolization coil 50 that is distal of the proximal end of the first embolization coil 50.

In some embodiments, the first pushing member 420 has a portion that extends into the coil lumen 56 of the first embolization coil 50 and provides straightening support to the first embolization coil 50. For example, the first pushing member 420 may provide straightening support such that when the first embolization coil 50 is pushed out of the lumen 408, the first pushing member 420 resists the configuring of a portion of the first embolization coil 50 from an insertable configuration into a deployed configuration.

A first coupling member 432 may be coupled to a proximal portion of the first embolization coil 50 and extend through the coil lumen 66 of the second embolization coil 60 and a lumen defined by the second pushing member 426. Similarly, a second coupling member 438 may be coupled to a proximal portion of a second embolization coil 60 and extend through a lumen defined by the second pushing member 426. Similar to the coupling members 160 and 360 discussed in the described embodiments above, first and second coupling members 432 and 438 may be coupled to the first and second embolization coils 50 and 60 in any number of ways, as will be appreciated by one of ordinary skill in the art.

In some instances, a first retaining member 444 couples a proximal portion of the first coupling member 432 to the first pushing member 420. Similarly, a second retaining member 450 may retain a proximal portion of the second coupling member 438 to a proximal portion of the second pushing member 426, such as a proximally-facing surface of the second pushing member 426. The first and second retaining members 444 and 450 may retain portions of the first and second coupling members 432 and 438 in the proximal end region of the coil delivery system 400 so that portions of the first and second coupling members 432 and 438 are accessible to an operator of the coil delivery system 400. In some instances, the first and second retaining members 444 and 450 are slidably coupled to the first and second coupling members 432 and 438.

Figure 5:
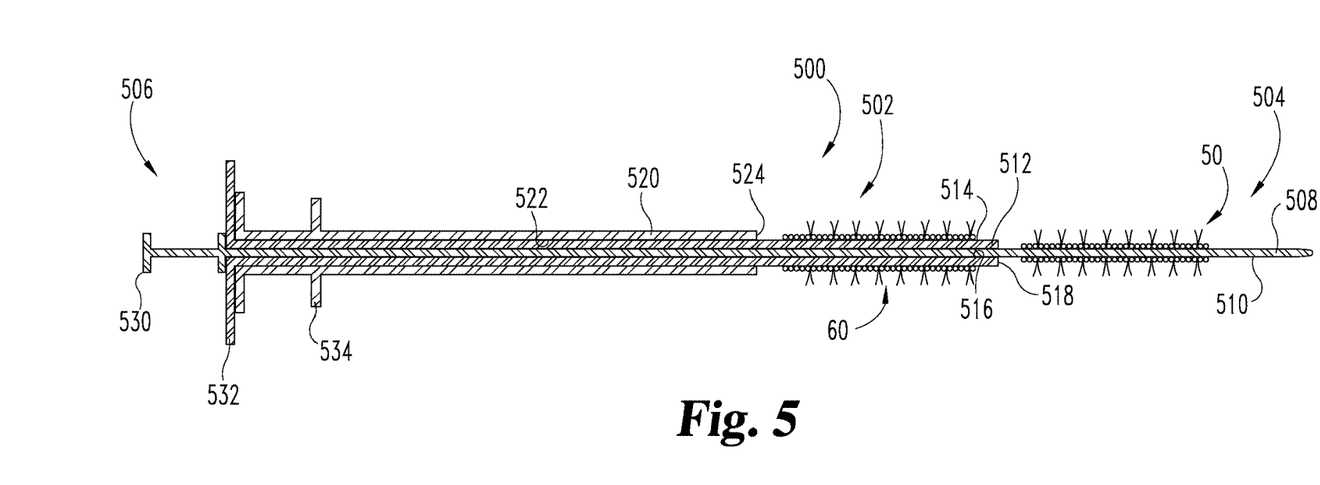
FIG. 5 illustrates an embodiment of an embolization coil delivery system.

FIG. 5 illustrates an embodiment of a coil delivery system 500 where a first embolization coil 50 and a second embolization coil 60 are positioned around straightening members. In this embodiment, the coil delivery system 500 comprises an elongated body 502 having a distal end region 504, a proximal end region 506, a first straightening member 508, and a second straightening member 512. The first straightening member 508 extends through the coil lumen 56 of the first embolization coil 50 in an insertable configuration and has a surface 510 on which the first embolization coil 50 is positioned on. Similarly, the second straightening member 512 extends through the coil lumen 66 of the second embolization coil 60 and has an outer surface 514 on which the second embolization coil 60 is positioned on.

The first straightening member 508 extends through a lumen defined by an inner surface 516 of the second straightening member 512. The inner surface 516 of the second straightening member 512 is slidably coupled to the surface 510 of the first straightening member 508, allowing the first straightening member 508 to move independently of the second straightening member 512.

The second straightening member 512 has a pushing surface 518 on a distal portion of the second straightening member 512. The pushing surface 518 is arranged to contact a proximal portion of the first embolization coil 50 so as to push the first embolization coil 50 distally along a length of the first straightening member 508 and past the distal end of the first straightening member. After a portion of the first embolization coil 50 is moved past the distal end of the first straightening member 508, it can configure from an insertable configuration into a deployed configuration to provide support for a subsequently deployed embolization coil and/or to occlude a vessel within the body of the patient.

An outer sheath 520 has an inner surface 522 defining an inner lumen arranged to receive the second straightening member 512. The inner surface 522 is arranged to slidably couple with the outer surface 514 of the second straightening member 512 so as to allow the second straightening member 512 to move independently of the outer sheath 520, such as by sliding along a proximal-distal direction within the outer sheath 520. Additionally, the outer sheath 520 has a pushing surface 524 similar to the pushing surface 518 of the second straightening member 512. The pushing surface 524 of the outer sheath 520 is arranged to push against a proximal portion of the second embolization coil 60 so as to push portions of the second embolization coil 60 in a distal direction along a length of the second straightening member 512 and past the distal end of the second straightening member 512.

In some instances, the coil delivery system 500 has handles 530, 532, and 534 positioned near the proximal end region 506 of the coil delivery system 500. The handles 530, 532, and 534 can be arranged such that they allow the independent manipulation of the first straightening member 508, the second straightening member 512, and/or the outer sheath 520 of the coil delivery system 500. In some instances, the handles 530, 532, and 534 are arranged to be grasped with a hand of an operator and/or the handles 530, 532, and 534 can be arranged to be operated with an additional device such as a control and/or triggering mechanism to control the release of the first and/or second embolization coils 50, 60.

In some instances, the coil delivery system 500 further comprises coupling members, such as coupling members 160, 360, 432, and 438 described above, that allow for greater control of the embolization coils 50 and 60 prior to and/or after release from the straightening members 508 and 512. Additionally, retaining members, such as first and second retaining members 444 and 450 described above, may be used to retain portions of the coupling members.

The coil delivery system 500 may also comprise additional straightening members and or sheaths to facilitate the insertion of the coil delivery system 500 into the body of a patient and/or to accommodate additional embolization coils on the coil delivery system 500. For example, a second sheath may be positioned around the outer sheath 520 as well as the first and second embolization coils 50 and 60. The second sheath may protect the first and second embolization coils 50 and 60 from movement along the first and second straightening members 508 and 512 during the positioning of the coil delivery system 500 within the body of a patient and prior to independent movement of the first straightening member 508, second straightening member 512, and/or outer sheath 520. In some instances, the second sheath, such as a tear-away sheath, may be removed prior to deployment of the embolization coils.

Figure 6:
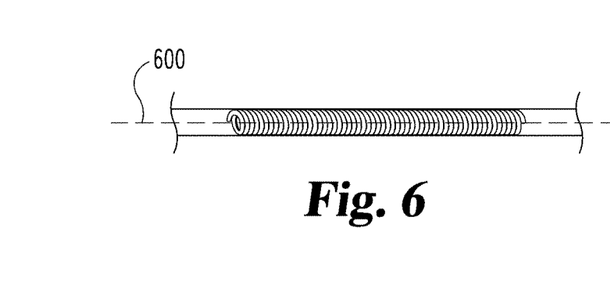
FIGS. 6 and 7 illustrate embodiments of embolization coils loaded in delivery systems.
Figure 7:
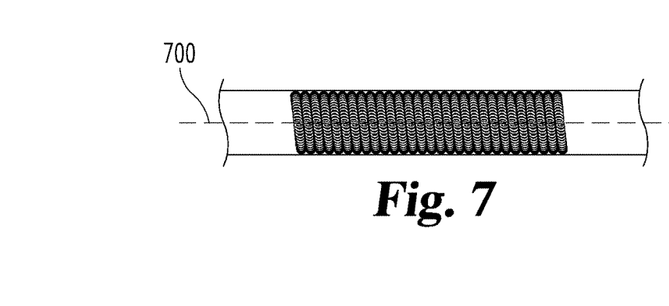

FIGS. 6 and 7 illustrate two insertable configurations of the embolization coils. The first and/or second embolization coils 50, 60 may be positioned within a lumen of a coil delivery system and/or around a straightening member of a coil delivery system in these configurations. In FIG. 6, the embolization coil is in a configuration in which the wire portion of the embolization coil is helically coiled around a longitudinal axis 600. In FIG. 7, the embolization coil is coiled twice. For example, the wire portion of the embolization coil may be first coiled once around a first longitudinal axis, and then coiled again around a second longitudinal axis 700 such that the lumen defined by the first coiling follows a helical path around the second longitudinal axis 700.

As will be appreciated by one of ordinary skill in the art, the above description is not limited to the illustrated and described embolization coil configurations. The embolization coils may form a number of insertable configurations and/or deployed configurations not explicitly disclosed herein but that will be apparent to one of ordinary skill in the art.

Additionally, features illustrated and described in the above embodiments are not intended to be limited to those embodiments. Features from different embodiments above may be combined. For example, one or more embolization coils may be deployed from within a lumen, such as outer cannula lumen 116 in FIG. 1, with one or more embolization coils being deployed from a straightening member, such as first straightening member 508 illustrated in FIG. 5, to name one non-limiting example. Similarly, a coil delivery system may have more catheters, cannulas, pushers, and/or coupling members than those illustrated and described above. In some embodiments these members may be in coaxial arrangement or in a parallel, side-by-side arrangement, to name a few non-limiting examples.

It should be appreciated that the coil delivery systems illustrated above may be constructed from any materials apparent to one of ordinary skill in the art. For example, the coil delivery system may have portions constructed of metal and/or a polymer, to name a few non-limiting examples. In some cases, a multipurpose catheter constructed from a polymer can be used for cannulas, such as 104, 304, and/or catheters, such as 402, described above. Similarly, a wire guide and/or a wire pusher used in some existing embolization coil delivery systems may be used for the pushing member, such as 150, and/or the straightening member, such as 508.

In some instances, the embolization coils, such as 50 and 60, are preloaded in the coil delivery system. For example, the coil delivery system provided to a doctor or physician may already have the selected embolization coils positioned therein in their insertable configuration. In other instances, the embolization coils are provided separately from the coil delivery system and are loaded into the coil delivery system prior to insertion into the body. For example, the embolization coils may be provided in one or more cartridges which are then coupled to the coil delivery system, and the embolization coils are transferred from their cartridges into the coil delivery system. In some embodiments, the embolization coils are provided in the coil delivery system which itself serves as a cartridge with is combined with a manipulating mechanism to manipulate various portions of the coil delivery system to deploy one or more embolization coils.

In some embodiments, the coil delivery system is supplied in a sterilized package, such as a peel-open package. The coil delivery system may be packaged with embolization coils (preloaded or not), needles, guide wires, introducers, dilators, syringes, and/or other devices that may be used before, during, and/or after deploying the embolization coils within the body of a patient.

In some embodiments, the first embolization coil 50 and the second embolization coil 60 have different physical dimensions. For example, the first embolization coil 50 may have a different length than the second embolization coil 60. In some instances, the wire portions of the first and second embolization coils 50 and 60 have different wire thicknesses. Similarly, the first embolization coil 50 and second embolization coil 60 may have a different maximum outer diameter in their insertable and/or deployed configurations. Furthermore, the first and second embolization coils 50 and 60 may have a different frequency of turns in the coils in their insertable and/or deployed configurations.

In some instances, the first and second embolization coils 50 and 60 have different properties. For example, the first and second embolization coils 50 and 60 may have different magnetic properties and/or radiological properties. This may aid in the deployment of the embolization coils 50, 60 and/or with the subsequent identification of the embolization coils. In some embodiments, the embolization coils 50, 60 have different strength and/or deformability. For example, the first embolization coil 50 may be a "soft" coil having a lower stiffness than the second embolization coil 60.

One way of having different properties between the first and second embolization coils 50, 60 is by constructing the first and second embolization coils 50, 60 from different materials. In some instances, the first and second embolization coils 50, 60 are constructed of compositionally different metals, such as different elemental metals or different metal alloys. For example, the first embolization coil 50 may be made of an austenitic nickel-chromium-based superalloy, such as the material sold under the mark Inconel® and made by the Special Metals Corporation, and the second embolization coil 60 may be made of platinum. Certain materials may be selected due to their properties and the desired properties of the constructed embolization coil; however, materials may also be selected for other considerations, such as the ease, reliability, and or methods of manufacturing.

The physical dimensions, properties, and/or materials of the embolization coils 50 and 60 may not only differ between the embolization coils 50 and 60 but may also vary along the length of an embolization coil 50 or 60. For example, one portion of the first embolization coil 50 may have a different frequency of turns than another portion, or one portion of the first embolization coil 50 may have a different stiffness than another portion.

As will be appreciated by one of ordinary skill in the art, the embolization coils 50, 60 may be made of metal and/or magnetic resonance (MR) safe or MR conditional materials such that the embolization coil 50 and/or 60 may be easily detected radiographically but with little or no ferro-magnetic properties. In some instances, one or more of the embolization coils may be MRI compatible. Additionally, the embolization coils can be coated, such as with a polymerized tetrafluoroethylene, and can have fibers, such as synthetic fibers, to aid in occluding a portion of the aneurysm and/or vessel.

Methods of Use

Figure 8:
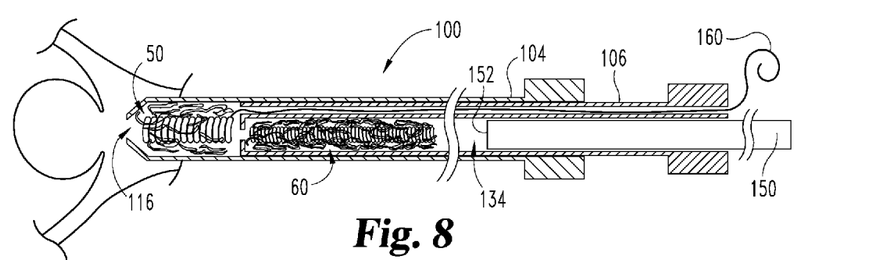
FIGS. 8, 9, 10, and 11 illustrate a method of using an embolization coil delivery system, such as the system illustrated in FIGS. 1 and 2.
Figure 9:
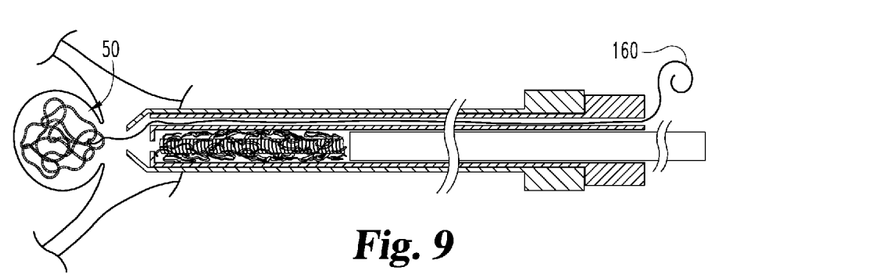
Figure 10:
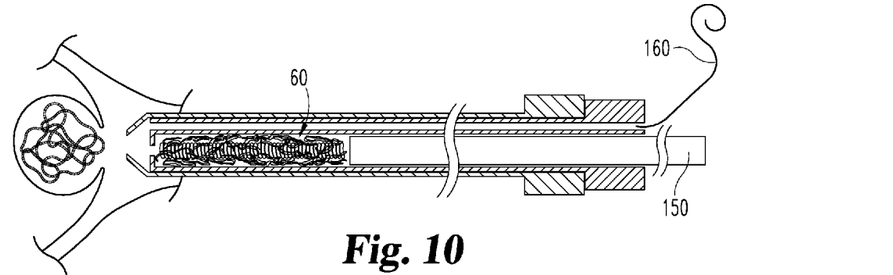
Figure 11:
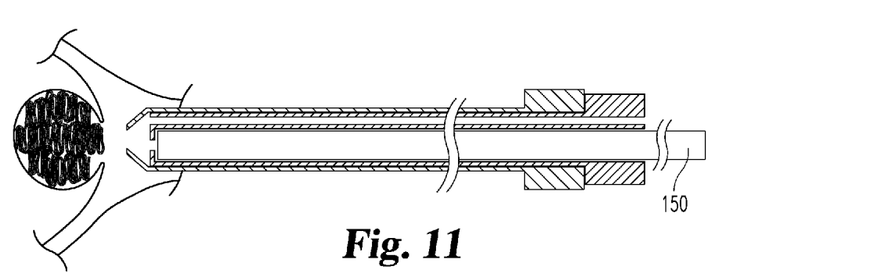

FIGS. 8, 9, 10, and 11 illustrate a method of using a coil delivery system, such as the coil delivery system 100 illustrated in FIGS. 1 and 2. As shown in FIG. 8, the coil delivery system 100 is advanced to a target location within the body of a patient. As the inner cannula 106 of the coil delivery system 100 is advanced distally relative to the outer cannula 104, a distal portion of the inner cannula 106 contacts a proximal portion of the first embolization coil 50 and pushes the first embolization coil 50 distally out of the outer cannula lumen 116 of the outer cannula 104. The coupling member 160 may be detached from the first embolization coil 50, such as when an operator is satisfied that the first embolization coil 50 is sufficiently positioned within the target location of the patient. (Illustrated in FIG. 10)

The second embolization coil 60 may then be deployed by advancing the pushing member 150 in a distal direction within the coil lumen 134 of the inner cannula 106. The pushing surface 152 of the pushing member 150 contacts a proximal portion of the second embolization coil 60 and pushes the second embolization coil 60 out of the distal end of the coil lumen 134 and the distal end of the outer cannula lumen 116 so as to deliver the second embolization coil 60 towards the location of the first embolization coil 50. (Illustrated in FIG. 11)

Figure 12:
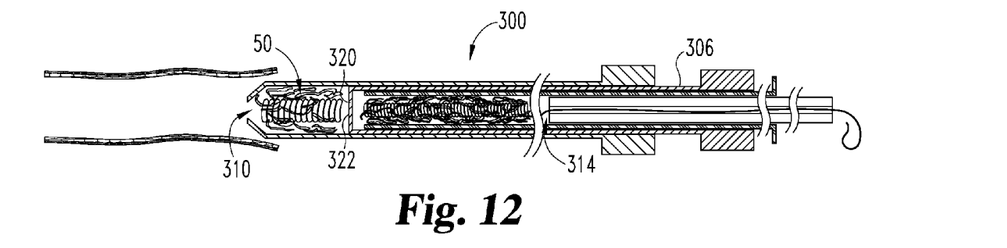
FIGS. 12, 13, 14, 15, and 16 illustrate a method of using an embolization coil delivery system, such as the system illustrated in FIG. 3.
Figure 13:
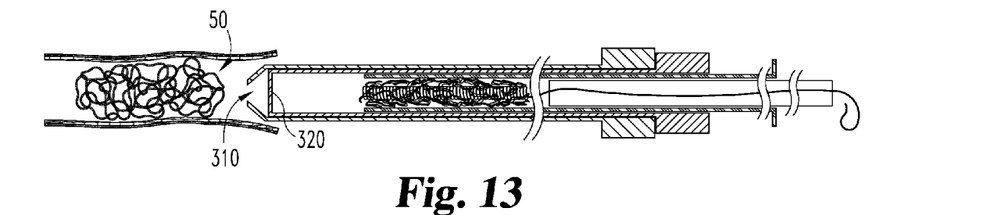
Figure 14:
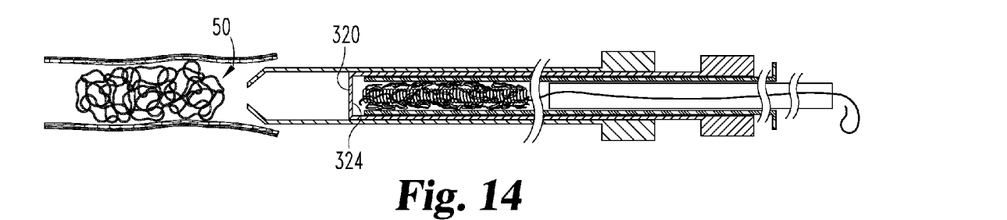
Figure 15:
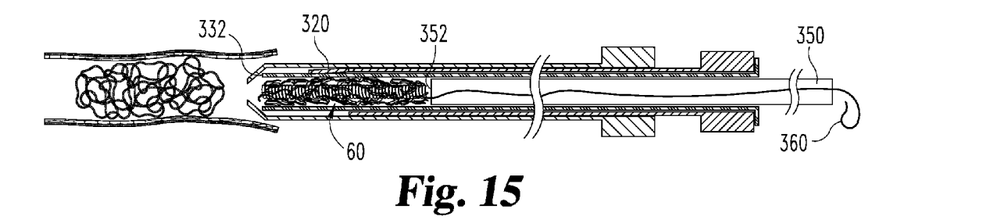
Figure 16:
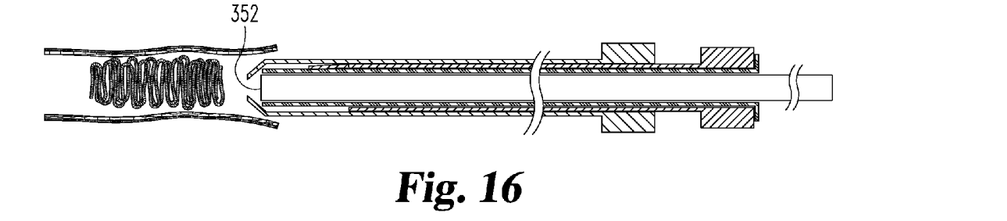
Figure 17:
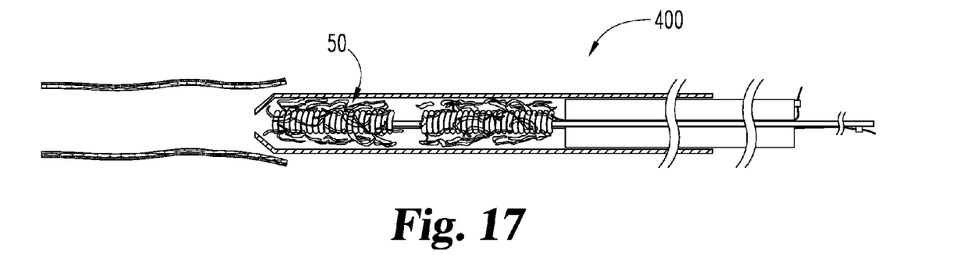
FIGS. 17, 18, 19, 20, and 21 illustrate a method of using an embolization coil delivery system, such as the system illustrated in FIG. 4.

FIGS. 12, 13, 14, 15, and 16 illustrate a method of using a coil delivery system, such as the coil delivery system 300 illustrated in FIG. 3. As illustrated in FIG. 12, the coil delivery system 300 is advanced to a target location within the body of a patient, such as a portion of a vessel. The intermediate cannula 306 is moved distally within the outer lumen 310 so as to contact a distal surface 322 of the door portion 320 against a proximal portion of the first embolization coil 50. As the intermediate cannula 306 is advanced distally through the outer lumen 310, the door portion 320 pushes the first embolization coil 50 out of the outer lumen 310 and into the target location within the body of the patient. (Illustrated in FIG. 13) After the first embolization coil 50 has been deployed, the intermediate cannula 306 may then be withdrawn in a proximal direction within the outer lumen 310 so as to allow for the opening of the door portion 320 to communicate the outer lumen 310 and the inner lumen 314. (Illustrated in FIG. 14) After the intermediate cannula 306 is in a withdrawn position, the inner cannula 308 is advanced in a distal direction and the pushing surface 332 of the inner cannula 308 contacts the proximal surface 324 of the door portion 320 pushing the door portion 320 into an open configuration. FIG. 15 illustrates the coil delivery system after the inner cannula 308 has pushed the door portion 320 of the intermediate cannula 306 into an open configuration. The pushing member 350 may then be advanced distally within the inner lumen 314. The pushing surface 352 contacts a proximal portion of the second embolization coil 60 so as to push the second embolization coil 60 through the inner lumen 314 of the inner cannula 308 and out of the distal end of the coil delivery system 300. In some instances, a coupling member 360 couples a portion of the second embolization coil 60 and may be detached after the second embolization coil 60 is advanced from the distal end of the coil delivery system 300.

Figure 18:
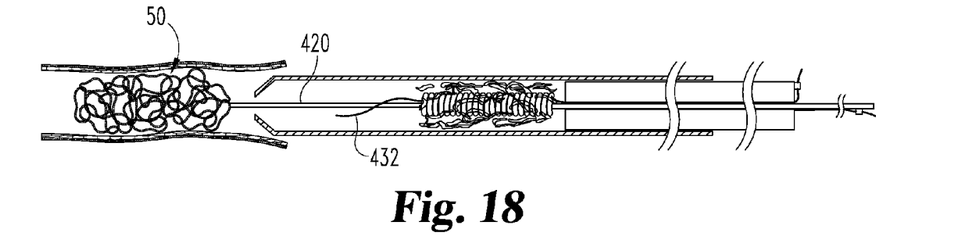
Figure 19:
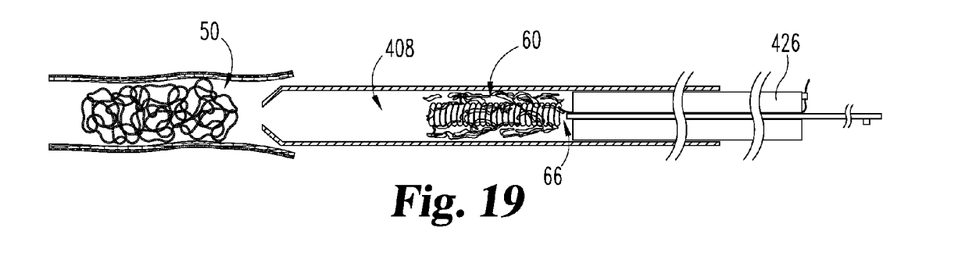
Figure 20:
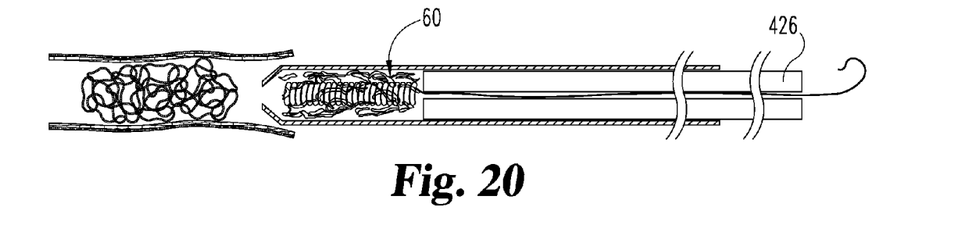
Figure 21:
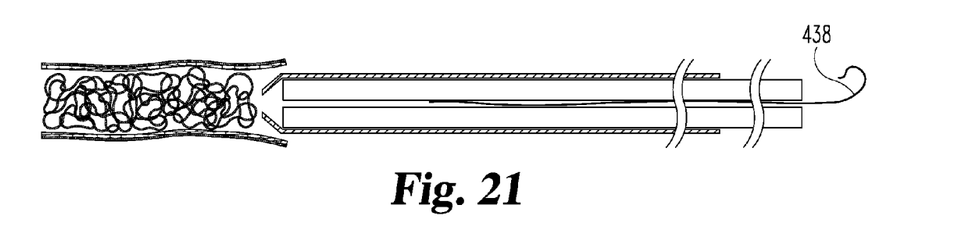

FIGS. 17, 18, 19, 20, and 21 illustrate a method of using a coil delivery system, such as the coil delivery system 400 illustrated in FIG. 4. Similar to the above description of the methods of using the embolization coils illustrated in FIGS. 1-3, in FIG. 17 the coil delivery system 400 is advanced to a target location within the body of a patient. In FIG. 18, the first embolization coil 50 is pushed out of a distal end region of the coil delivery system 400 by the first pushing member 420. The first coupling member 432 may be detached from a portion of the first embolization coil 50 so as to release the connection between the first embolization 50 and the coil delivery system 400. The first pushing member 420 may then be withdrawn through the coil lumen 66 of the second embolization coil 60, as illustrated in FIG. 19. FIG. 20 illustrates the advancement of the second embolization coil 60 in a distal direction within the lumen 408 of the coil delivery system 400 by the second pushing member 426 pushing on a portion of the second embolization coil 60. After the second pushing member 426 pushes the second embolization coil 60 out of the lumen 408, the second coupling member 438 may be detached from the second embolization coil 60 so as to completely detach the second embolization coil 60 from the coil delivery system 400.

Figures 22, 23:
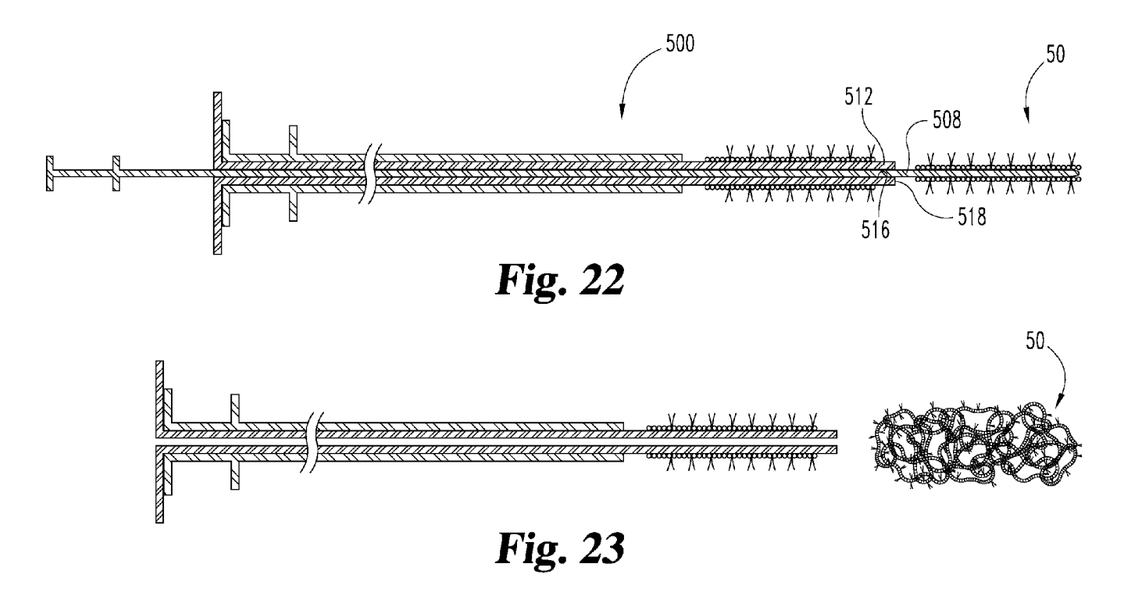
FIGS. 22, 23, 24, and 25 illustrate a method of using an embolization coil delivery system, such as the system illustrated in FIG. 5.
Figure 24:
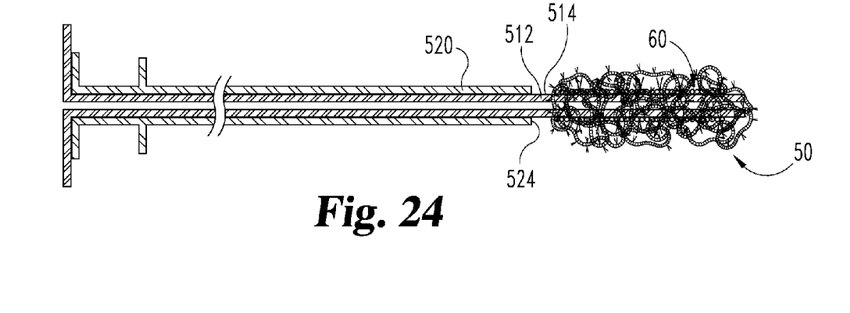
Figure 25:
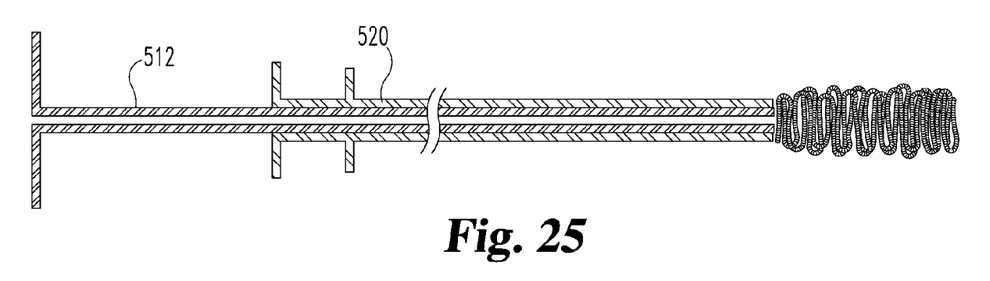

FIGS. 22, 23, 24, and 25 illustrate a method of using a coil delivery system, such as coil delivery system 500 illustrated in FIG. 5. The first straightening member 508 may be withdrawn in a proximal direction within the lumen defined by the inner surface 516 of the second straightening member 512. As the first straightening member 508 is withdrawn, a proximal portion of the first embolization coil 50 contacts the pushing surface 518 of the second straightening member 512 and the pushing surface 518 pushes the first embolization coil 50 distally along the length of the first straightening member 508. As portions of the first embolization coil 50 are removed from the first straightening member 508, the first embolization coil 50 transitions from a first configuration into a second configuration, the second configuration being a deployed configuration such as illustrated in FIG. 23. After the first embolization coil 50 is deployed, the coil delivery system 500 and/or the second straightening member 512 may be repositioned so as to locate the second embolization coil 60 selectively within the area of the first embolization coil 50. (Illustrated in FIG. 24) When the second embolization coil 60 is in position within the area of the first embolization coil 50, the second straightening member 512 is withdrawn in a proximal direction from within the lumen defined by the outer sheath 520. The pushing surface 524 of the outer sheath 520 contacts a proximal portion of the second embolization coil 60 and pushes the second embolization coil 60 in a distal direction relative to the second straightening member 512. As the second embolization coil 60 is pushed off of the outer surface 514 of the second straightening member 512, the second embolization coil 60 transitions from a first configuration into a second configuration. (Illustrated in FIG. 25)

Figure 26:
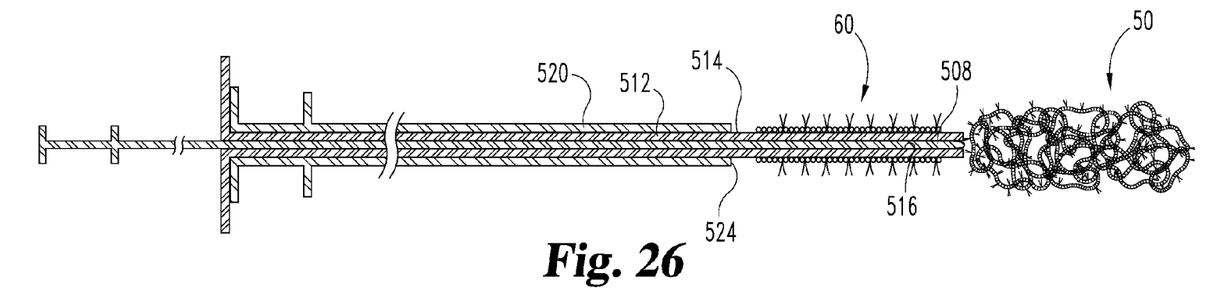
FIGS. 26 and 27 illustrate an alternative method of using an embolization coil delivery system, such as the system illustrated in FIG. 5.
Figure 27:
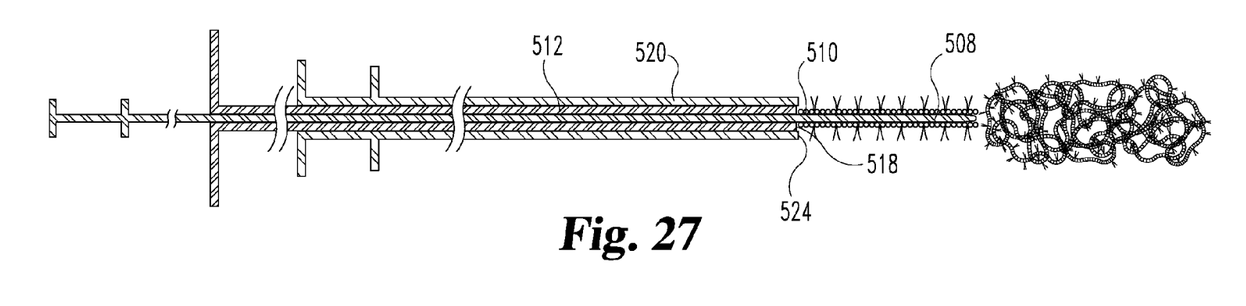

FIGS. 26 and 27 illustrate an alternative method of deploying the second embolization coil 60 from a coil delivery system, such as the coil delivery system 500. As illustrated in FIG. 26, the first straightening member 508 may be left within the lumen defined by the inner surface 516 of the second straightening member 512 after deployment of the first embolization coil 50. The second embolization coil 60 is then moved from the outer surface 514 of the second straightening member 512 onto the surface 510 of the first straightening member 508. For example, the second straightening member 512 may be withdrawn in a distal direction relative to the outer sheath 520 and the first straightening member 508. The pushing surface 524 of the outer sheath 520 pushes against a proximal portion of the second embolization coil 60 so as to push the second embolization coil 60 off of the outer surface 514 and onto the surface 510 of the first straightening member 508.

The coil delivery system 500 and a portion therefore, such as the first straightening member 508, may then be advanced into the area of the first embolization coil 50 so as to position the second embolization coil 60 for deployment in the area of the first embolization coil 50. Then, similar to the deployment of the first embolization coil 50 off of the first straightening member 508, the second embolization 60 may be deployed from the first straightening member 508 by withdrawing the first straightening member 508 in a proximal direction relative to the second straightening member 512 with the pushing surface 518 of the second straightening member 512 pushing on a portion of the second embolization coil 60 so as to push the second embolization coil 60 off of the first straightening member 508.

While at least one embodiment has been illustrated and described in detail in the drawings and foregoing description, the same is to be considered as illustrative and not restrictive in character, it being understood that preferred embodiments have been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A multi-embolization coil delivery system, comprising:
an elongated body retaining a first embolization coil, a second embolization coil, a first pushing member, and a second pushing member;
wherein said first embolization coil is pushably coupled to said first pushing member, said first pushing member having a distally facing surface arranged to push said first embolization coil from said elongated body, and said second embolization coil is pushably coupled to said second pushing member, said second pushing member having a distally facing surface arranged to push said second embolization coil from said elongated body;
wherein said first pushing member is independently manipulable of said second pushing member;
wherein said second pushing member extends through a lumen of said first pushing member; and
wherein said first embolization coil and said second embolization coil are longitudinally spaced so as to not overlap along a length of said delivery system when said first and second embolization coils are retained by said elongated body.

2. The delivery system of claim 1, wherein said second embolization coil is positioned in said lumen of said first pushing member.

3. The delivery system of claim 1, wherein:
said first and second embolization coils are capable of movement independent of one another.

4. The delivery system of claim 1, wherein:
said first embolization coil and said second embolization coil are constructed of different materials.

5. The delivery system of claim 4, wherein:
said first embolization coil and said second embolization coil are constructed of different metals.

6. The delivery system of claim 5, wherein:
at least one of said first or second embolization coils is constructed of an austenitic nickel-chromium-based superalloy.

7. The delivery system of claim 1, wherein:
said first embolization coil is a scaffold embolization coil.

8. The delivery system of claim 1, wherein:
said second pushing member comprises a wire pusher.

9. The delivery system of claim 1, comprising:
a coupling member coupled to said first embolization coil and arranged to withdraw a deployed portion of said first embolization coil back to said elongated body.

10. A multi-embolization coil delivery system, comprising:
an elongated body arranged to retain a first embolization coil and a second embolization coil;
a first pushing member having a distally facing surface arranged to push said first embolization coil from said elongated body; and
a second pushing member having a distally facing surface arranged to push said second embolization coil from said elongated body;
wherein said delivery system is operable to move said first embolization coil independently of said second embolization coil;
wherein said second pushing member extends through a lumen of said first pushing member; and
wherein said first embolization coil and said second embolization coil are longitudinally spaced so as to not overlap along a length of said delivery system when said first and second embolization coils are retained by said elongated body.

11. The delivery system of claim 10, further comprising:
a first lumen defined by an outer cannula of said elongated body;
said first embolization coil and first pushing member positioned in said first lumen said second embolization coil positioned in said lumen of said first pushing member.

12. The delivery system of claim 10, wherein:
said first embolization coil and said second embolization coil are constructed of different materials.

13. The delivery system of claim 12, wherein:
said first embolization coil and said second embolization coil are constructed of different metals.

14. The delivery system of claim 13, wherein:
at least one of said first or second embolization coils is constructed of an austenitic nickel-chromium-based superalloy.

15. The delivery system of claim 10, wherein:
said first embolization coil is a scaffold embolization coil.

16. The delivery system of claim 10, wherein said distally facing surface of said first pushing member is positioned distally of a distal end of said second embolization coil when said first and second embolization coils are positioned within said elongated body.

17. A multi-embolization coil delivery system, comprising:
an elongated body defining a first lumen;
a detachable first embolization coil positioned in said first lumen distal of a first pushing member positioned in said first lumen;
said first pushing member defining a second lumen; and
a detachable second embolization coil positioned in said second lumen distal of a second pushing member positioned in said second lumen; and
wherein said first embolization coil has a proximal end positioned distally of a distal end of said second embolization coil when said first and second embolization coils are positioned within said elongated body.

18. The delivery system of claim 17, wherein:
said first embolization coil and said second embolization coil are constructed of different materials.

19. The delivery system of claim 18, wherein:
said first embolization coil and said second embolization coil are constructed of different metals.

20. The delivery system of claim 19, wherein:
at least one of said first or second embolization coils is constructed of an austenitic nickel-chromium-based superalloy.

21. The delivery system of claim 17, wherein:
said first embolization coil is a scaffold embolization coil and is positioned distally of said second embolization coil.

22. The delivery system of claim 17, wherein said first pushing member has a distal end positioned distally of said distal end of said second embolization coil when said first and second embolization coils are positioned within said elongated body.

* * * * *